United States Patent [19]
John

[11] Patent Number: 5,437,198
[45] Date of Patent: Aug. 1, 1995

[54] UNIVERSAL IMPACTOR FOR PARTICLE COLLECTION WITHIN SAMPLING CRITERIA

[76] Inventor: Walter John, 2329 Fourth St., Berkeley, Calif. 94710

[21] Appl. No.: 223,660

[22] Filed: Apr. 6, 1994

[51] Int. Cl.⁶ .............................................. G01N 1/00
[52] U.S. Cl. .................................................. 73/863.22
[58] Field of Search ........................... 73/28.04–28.06, 73/863.22; 55/270

[56] References Cited

U.S. PATENT DOCUMENTS

| | | | |
|---|---|---|---|
| 2,538,116 | 1/1951 | May | 73/28.04 |
| 3,518,815 | 7/1970 | McFarland et al. | 73/863.22 |
| 4,133,202 | 1/1979 | Marple . | |
| 4,350,507 | 9/1982 | Greenough et al. . | |
| 4,400,982 | 8/1983 | Bell . | |
| 4,452,068 | 6/1984 | Loo . | |
| 4,463,595 | 8/1984 | Yeh et al. . | |
| 4,670,135 | 6/1987 | Marple et al. . | |
| 4,764,186 | 8/1988 | Langer | 73/28.06 |
| 4,972,957 | 11/1990 | Liu et al. . | |
| 5,040,424 | 8/1991 | Marple et al. . | |

OTHER PUBLICATIONS

Air Sampling Procedures Committee: Particle Size-Selective Sampling in the Workplace. American Conference of Governmental Industrial Hygienists, Cincinnati, Ohio (1985).
U.S. Environmental Protection Agency: Revisions to the National Ambient Air Quality Standards for Particulate Matter. Fed. Reg. 52:24634–24750 (1987).
Davies, C. N. Dust Sampling and Lung Disease, Br. J. Ind. Med. 9:120 (1952).
Marple, V. A., Simulation of Respirable Penetration Characteristics by Inertial Impaction. J. Aerosol Sci. 9, 125–134, (1978).
American Conference of Governmental Industrial Hygienists: Threshold Limit Values for Chemical Substances and Physical Agents and Biological Exposure Indices, 1993–1994, Cincinnati, Ohio.
Marple et al., Personal Sampling Impactors With Respirable Aerosol Penetration Characteristics, Am. Ind. Hyg. Assoc. J. 44:916–922 (1983).
Tomb et al., A New Two-Stage Respirable Dust Sampler. Am. Ind. Hyg. Assoc. J. 36:1 (1975).

Primary Examiner—Robert Raevis
Attorney, Agent, or Firm—James Creighton Wray

[57] ABSTRACT

A universal impactor for sampling airborne particles has a slit nozzle that tapers in width along its length. The slit nozzle is in a plate that is thicker near wide parts of the slit and is thinner near narrow parts of the slit. An impaction plate beneath the slit is wider below wide parts of the slit and narrower below narrow parts of the slit. The impaction plate is sloped so that the impaction surface is at a greater distance below wide parts of the slit, and at a lesser distance below narrow parts of the slit. A passage adjacent to the impaction plate allows penetration of unimpacted particles to a particle collector or sensor. An air mover provides flow through the apparatus. The impactor has a particle impaction efficiency that varies smoothly with particle size and a curve of particle penetration efficiency vs. particle size that closely meets any predetermined sampling criteria.

31 Claims, 6 Drawing Sheets

AIR FLOW

UNIVERSAL IMPACTOR FOR PARTICLE COLLECTION WITHIN SAMPLING CRITERIA

BACKGROUND OF THE INVENTION

The present invention is used for sampling airborne particles (aerosols) and for health hazard evaluation of airborne particles.

For the evaluation of the health hazard from airborne particles, various organizations and agencies recommend or require that particle sampling conform to particle size-selective criteria. Those criteria are based on estimates of the probabilities that particles will penetrate to specific regions of the respiratory system. For example, the American Conference of Industrial Hygienists (ACGIH) has defined sampling criteria for the inhalable particulate mass for particles entering the nose or mouth and penetrating to any region of the respiratory tract, the thoracic particulate mass for particles penetrating into the tracheobronchial and gas-exchange regions and the respirable particulate mass for particles penetrating into the gas-exchange region. Those criteria prescribe the percent collection vs. particle aerodynamic diameter. Other sampling criteria include that of the U.S. Environmental Protection Agency (USEPA) for sampling in ambient air, called PM10. The British Medical Research Council (BMRC) has established criteria for sampling pneumoconious-producing dusts.

Various sampling devices are used to approximate the various sampling criteria. A 10 mm Nylon cyclone is used for the ACGIH respirable fraction. A disadvantage of cyclones is that the sampling characteristics are relatively fixed and must be determined empirically. The BMRC criteria is based on a horizontal elutriator. Penetration characteristics of an elutriator can be predicted from theory. However, the horizontal elutriator is not practical for personal sampling. Therefore, in coal mines, the 10 mm cyclone is used, and a correction factor is applied to approximate the BMRC criterion. Various inlets have been empirically designed to satisfy the USEPA PM10 criteria, which does not conform to the characteristics of any standard type of sampler.

A multiplicity of sampling criteria exist. The criteria continue to change as organizations reconsider the problem to take into account advances in knowledge.

A need exists for a particle sampler which is capable of accurately sampling according to a preselected sampling criteria.

SUMMARY OF THE INVENTION

The present invention provides a sampler which samples with chosen particle size selective characteristics. The present sampler is created to satisfy any arbitrary sampling criterion. The sampler of the invention produces a smooth curve of particle collection efficiency vs. particle diameter fitting a desired curve.

For the present invention, an impactor is designed to have a predetermined particle collection efficiency as a function of particle diameter. The nozzle slit has a width varying along the length, producing a continuous fit to the desired efficiency curve. The shape of the nozzle is calculated from impactor theory. As an example, an impactor has been constructed for sampling the ACGIH respirable mass. Laboratory tests verify the impactor's usefulness. Slits are presented for sampling the ACGIH thoracic mass, the BMRC respirable mass and the USEPA PM10 mass. The slits can be scaled to accommodate any desired flow rate.

Prior art impactors have sharp cutoffs which do not conform to the more slowly varying efficiencies of the various sampling criteria. An approximate solution to the problem was devised by Marple, who used a number of nozzles of different sizes in a single stage impactor. The collection efficiency of the Marple device was a stair step function of particle size, roughly approximating the smooth curve representing the sampling criterion.

The present invention provides an impactor having a nozzle in the form of a slit which is shaped so as to produce particle collection characteristics that vary smoothly with particle size to conform to almost any preselected sampling criteria. The shape of the slit is calculated from impactor theory. The slit has a width that tapers along the length of the slit. Where the slit is wide, the air flow is slow, allowing relatively larger particles to penetrate past the impaction plate. Where the slit is narrow, the air flow is faster and the penetrating particles are relatively smaller. The present invention has been constructed and has been tested in the laboratory. The slit plate is bevelled so that it is thicker near the central wide opening and thinner at the outer ends of the openings. An impaction plate beneath the slit is wide at its center and narrow at its opposite ends, and is placed at a distance from the slit plate greater at the center and less at the ends. The slit plate is mounted in a supporting disc. An outlet tube leads to a filter and then to a vacuum pump.

The slit plate assembly provides characteristics which closely meet existing sampling criteria from several sources.

A preferred airborne particle sampling apparatus has a support having a central opening. A slit plate is mounted on the support. The slit plate has a tapered slit for passing particles of various sizes through the slit. Unwanted particles flowing through the slit impact on an impaction plate connected to the support below the slit plate, removing them from the air stream. Unimpacted particles follow the air flowing past the impaction surface in a passage adjacent to the impaction plate. The penetration efficiency past the impaction plate is the sampling efficiency of the apparatus. Preferably a filter is connected to the support for collecting particles penetrating past the impaction plate. The filter could be replaced by a particle counter or other particle sensing device.

Preferably the tapered slit smoothly tapers from a large end to a small end.

In a preferred embodiment, the tapered slit smoothly tapers from remote small ends to a central large end.

Preferably the tapered slit is symmetrical about a first axis extending between ends of the slit and is symmetrical about a second axis perpendicular to the first axis.

The slit plate is bevelled from a thick part having a larger slit opening to a thin part having a smaller slit opening.

In a preferred embodiment, the impaction plate has a sloped impaction surface which is spaced a comparatively greater distance from a wide part of the tapered slit, and a comparatively smaller distance from a narrow end of the tapered slit. Preferably the impactor plate is relatively wider near a wide part of the tapered slit and it relatively narrower at a narrow end of the slit.

In one form of the invention, a slit nozzle has an impaction plate below it, followed by a filter and then an air mover.

These and other objects and features of the invention are apparent in the disclosure, which includes the above and ongoing written specification, with the claims and the drawings.

DETAILED DESCRIPTION OF THE DRAWINGS

Figure 1:
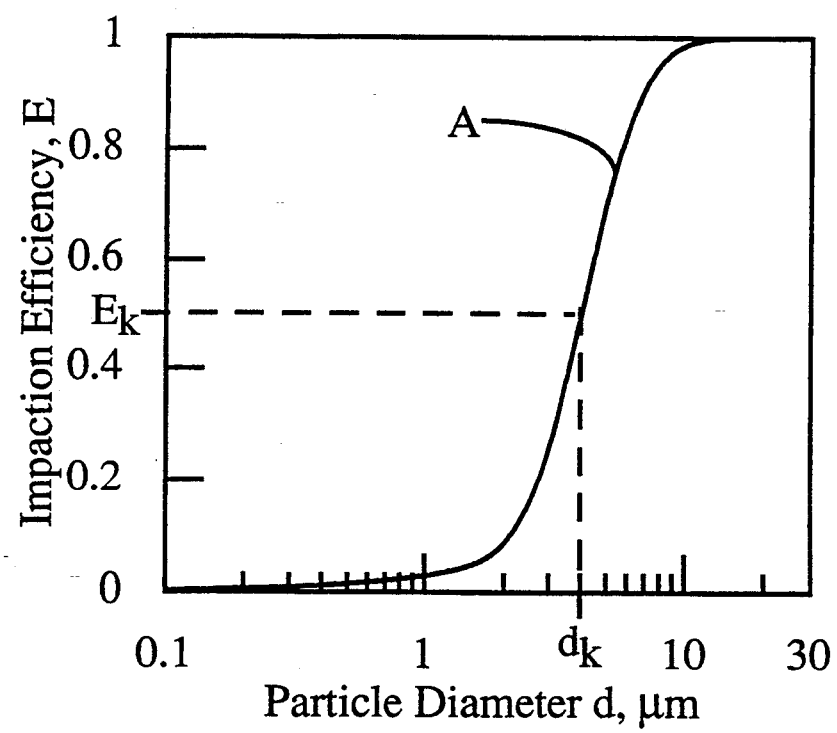
FIG. 1 is a plot of the impactor collection efficiency, E, vs. the dimensionless particle diameter, d/4.25.

Referring to the drawings, in FIG. 1 the impaction efficiency for the ACGIH respirable mass criteria vs. particle diameter is shown as curve A. The procedure for the design and construction of a universal impactor to fit the ACGIH respirable mass criteria is presented here as an example. The procedures can be applied to other particulate mass sampling criteria. The current ACGIH respirable mass collection efficiency, SR, is:

$$SR = SI[1 - \text{cnorm} (\ln d/4.5)/\ln 1.5)]$$

d is the particle aerodynamic diameter in $\mu$m. "cnorm" is the cumulative normal. "cnorm" is the cumulative normal distribution function defined by:

$$\text{cnorm}(x) = \frac{1}{\sqrt{2\pi}} \int_{-\infty}^{x} e^{\frac{-t^2}{2}} dt$$

where $x = (\ln d/4.5)/\ln 1.5$. SI, the inhalable mass collection efficiency, is given by:

$$SI = 0.5[1 \times \exp(-0.06 \, d)]$$

The impactor collection efficiency for the collection of particles on the impaction plate, E, is given by $E = 1 - SR$. E is plotted as a function of d in FIG. 1. E is divided into 1,000 equal increments. A large number of increments is taken so that each increment is very small, producing an essentially smooth curve. Each increment represents an increment of the slit having a width such that the cutpoint diameter corresponds to that on the curve. In FIG. 1, the kth increment $E_k$ corresponds to particle diameter $d_k$.

The width, $W_k$, of the kth slit increment is given by:

$$W_k = d_k^2 v \, C \rho_p / (9 \mu \, St_{50})$$

where v is the flow velocity, C is the Cunningham slip factor, $\rho_p$ is the particle material density, $\mu$ is the viscosity of air, and $St_{50}$ is the Stokes number given by $\sqrt{St_{50}} = 0.77$.

The length, $L_k$, of the kth slit increment is determined by the condition that each slit increment must have the same area:

$$L_k W_k = a$$

where a is a constant. Since the pressure drop is the same across each slit increment, the above condition provides that the flow rate through each increment will be the same, neglecting friction losses. k increases in the direction of decreasing particle diameter. Then, as k increases, $W_k$ decreases and $L_k$ increases. The accumulated length, $x_k$, along the slit to the midpoint of increment k is:

$$x_k = \sum_{1}^{k-1} L_j + L_k/2$$

The particle diameter at 50% collection efficiency is $D_{50} = 4$ $\mu$m, from the ACGIH criteria. A flow rate Q=2L/min is appropriate for a personal sampler. To simplify the selection of the remaining parameters, a simple rectangular slit of width $W_{50}$ and length L is considered. The following equations obtain for $W_{50}$, the aspect ratio b, and the Reynolds number Re:

$$W_{50} = D_{50}^2 C\rho_p/(9\mu\, St_{50}),\ b = L/W_{50},\ \text{and}\ Re = v\, W_{50}/0.15,$$

where $v = Q/(LW_{50})$.

Solving and substituting constants in cgs units:

$$b = 0.00553/W_{50}^3 \text{ and } Re = 40{,}300 W_{50}^2$$

The choice of $W_{50}$ determines b and Re, which vary in opposite directions with $W_{50}$. The aspect ratio b should be $>>1$ in order that the slit acts like a rectangular slit. Re should be greater than about 100 to minimize the variation of $St_{50}$ for the actual tapered slit. A compromise choice of $W_{50} = 0.08$ cm gives $b = 10.8$, $L = 0.86$ cm and $Re = 258$. The total slit area is 0.0688 $cm^2$. For the actual tapered slit, 50% efficiency is reached at $k = 500$; $W_{500} = 0.08$ cm and the total area$=0.0688$ $cm^2$ is adopted. That determines the constant a, which scales the slit length.

The ACGIH respirable curve B shown in FIG. 2 extends indefinitely on both the large and small particle ends. Since the impactor slit must be finite in length, the ends must be truncated. At the small particle end, because of the inverse relationship between $L_k$ and $W_k$, the slit increments become progressively longer. The length is truncated so that the penetration efficiency reaches 100% at 1.6 $\mu$m instead of 95% by the ACGIH criteria. If, for example, the choice were 100% at 0.5 $\mu$m instead of the criteria's 99%, the slit length would be increased by a factor of 1.6. The slit length for 95% efficiency is 1.06 cm. That was increased by 5% to 1.11 cm to correct for the missing 5%.

At the large particle end, the slit width increases rapidly with increasing particle diameter, producing a cusp. If the slope of the width vs. length curve became steep, the slit would lose the characteristics of a rectangular slit. The slit is truncated where the width, $W_{100}$, corresponds to a penetration efficiency of 10% at a particle diameter of 6.9 μm. To correct for the missing 10%, the slit was extended by 0.06 cm at a constant width equal to $W_{100}$. Due to an error, that added 20% to the area rather than 10%.

The compromises in performance from the slit truncations is less for slits designed for larger samplers, because the slits can be longer. Some sampling criteria, such as the BMRC and PM10 criteria, reach zero efficiency at a definite particle size, obviating the necessity of truncation at the large particle end. Also the infinite tails on the ACGIH respirable particulate mass criteria cannot be justified on the basis of health effects data.

Figure 2:
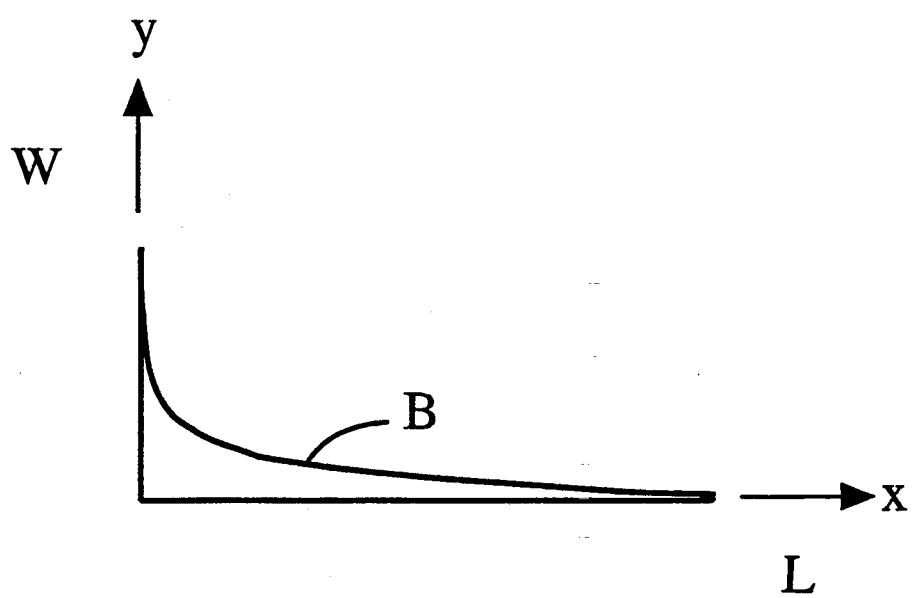
FIG. 2 shows a slit shape relationship for the ACGIH respirable mass.
Figure 3:
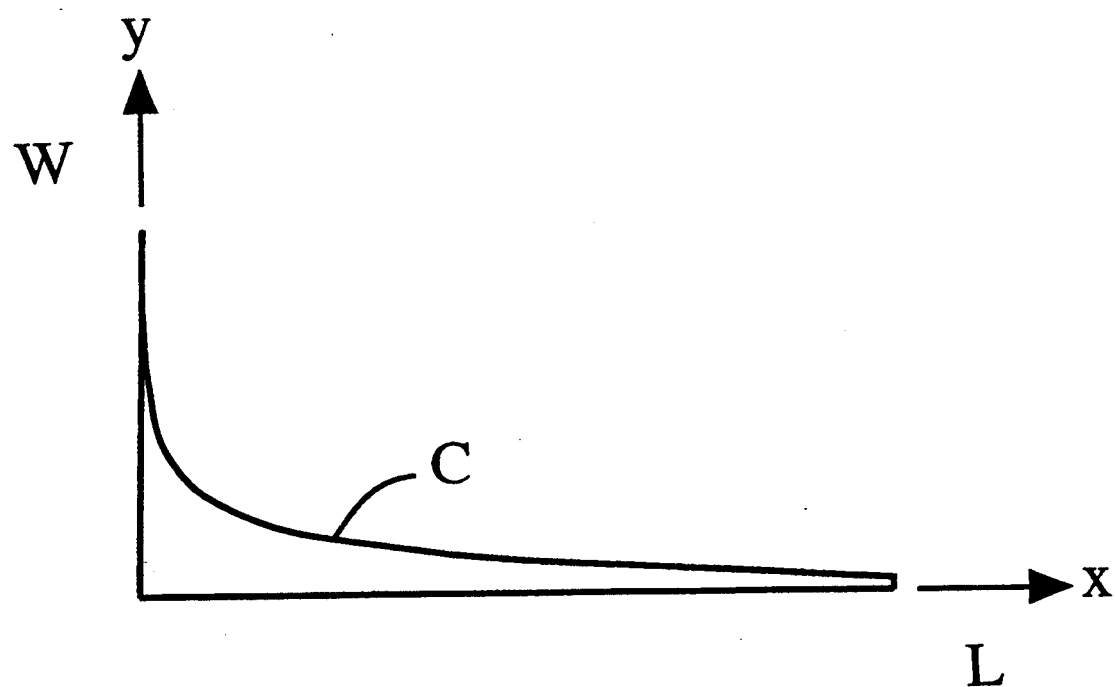
FIG. 3 shows slit shape relationship for the ACGIH thoracic mass.
Figure 4:
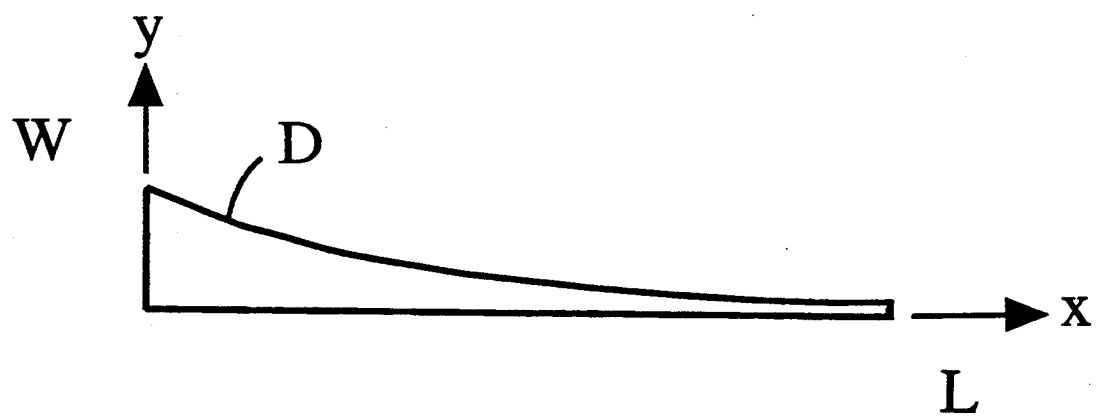
FIG. 4 shows slit shape relationship for the BMRC respirable mass.
Figure 5:
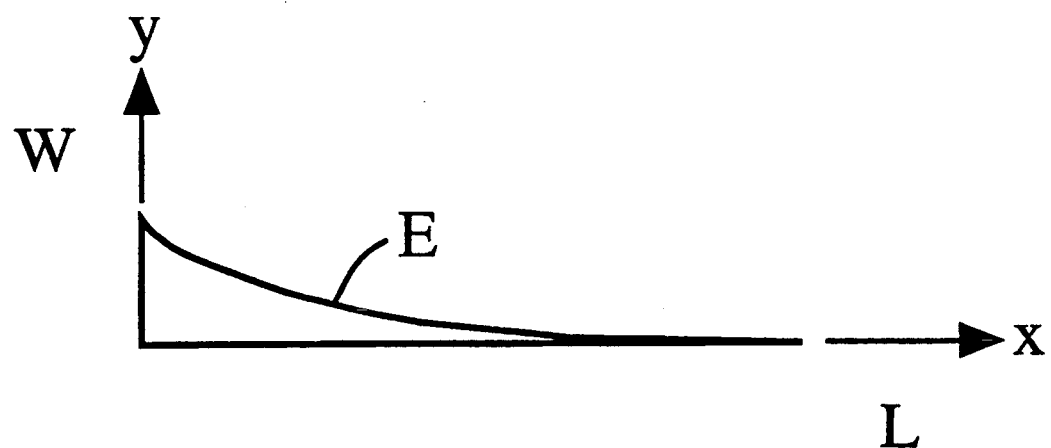
FIG. 5 shows a suitable slit shape relationship for the USEPA PM10 mass. The scales in FIGS. 1 through 5 are in arbitrary units.

The shape B of the slit for the ACGIH respirable mass criteria, i.e. the plot of slit width, W vs. length, L is shown in FIG. 2. The scales are in arbitrary units. The ACGIH thoracic mass criteria is similar to that for respirable except that the 50% cutpoint is 10 μm. The shape C of the slit for the ACGIH thoracic mass criteria is shown in FIG. 3. The dimensions shown for the width W and length L of the slit are in arbitrary units to show relationship of length to width. The curves D and E of the slits for the BMRC and PM10 criteria, respectively, are shown in FIGS. 4 and 5. In all cases the scale units are arbitrary units.

Figure 6:
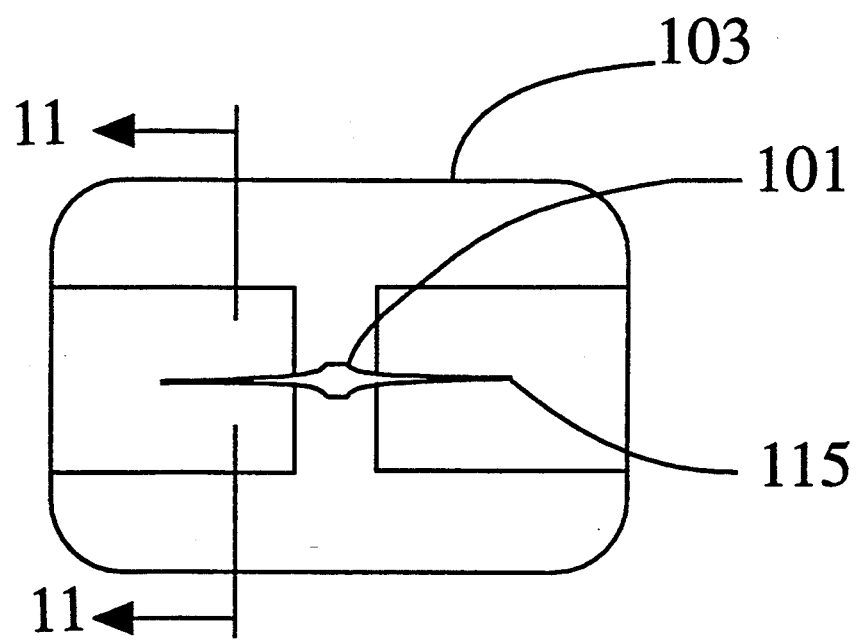
FIG. 6 shows a slit design for the ACGIH respirable particulate mass impactor. The scales are in arbitrary units, but the horizontal and vertical dimensions are in proportion.

To make the slit of the respirable mass particle universal impactor symmetrical, half of the width is placed above and half below a straight horizontal axis. (Because the slit is long compared to its width, the axis could be a circular arc, a spiral, or other curve.) Then the slit is reflected about a vertical axis on the large end. The result is the slit nozzle 101 shown in slit plate 103 in FIGS. 6 and 7. Since the area is doubled, the design flowrate is 4L/min. The slit and impaction plate assembly 105, the support disc 107 and the impaction plate 109 are shown in FIGS. 7 and 8.

The slit 101 is cut from a stainless steel blank 103 by electrical discharge machining (EDM). EDM affords high accuracy and resolution for machining a small slit. Any machining technique providing the necessary accuracy could be used. In EDM, the blank is mounted in an x-y carriage which is moved under digital computer control. An electrode or a fine wire, 0.0127 cm (0.005") diameter, is positioned along the z axis, is heated by electrical discharge and is moved vertically as the wire slices through the blank. The precision of the wire's x-y location is about 0.00025 cm (0.0001"). A computer file containing 3412 x-y coordinates was used to cut the slit. The steps in the x direction (long axis of the slit, FIG. 6) range from 0.0025 cm (0,001") at the narrow ends 115 to 0.00025 cm (0.0001") at the wide section in the center. The steps in the y direction (width, FIG. 6) range from 0.0013 cm (0.0005") or 17% of the width to 0,005 cm (0,002") or 4% of the width. The average errors in width are smaller because the carriage moves in a straight line between successive coordinates. The finished slit edge is smooth.

The x-y coordinates refer to the center of the wire; the cutting surface is displaced by the wire radius. That does not result in error because the blank is cut through along the horizontal axis with a small offset at the ends. When the halves are clamped together, the slit widths are exact. A small error is introduced because the curved slit edge does not contact the wire exactly at the end of the y-axis of the wire. However, the maximum error due to this effect is only 5% in width and hence can be neglected.

Figure 7:
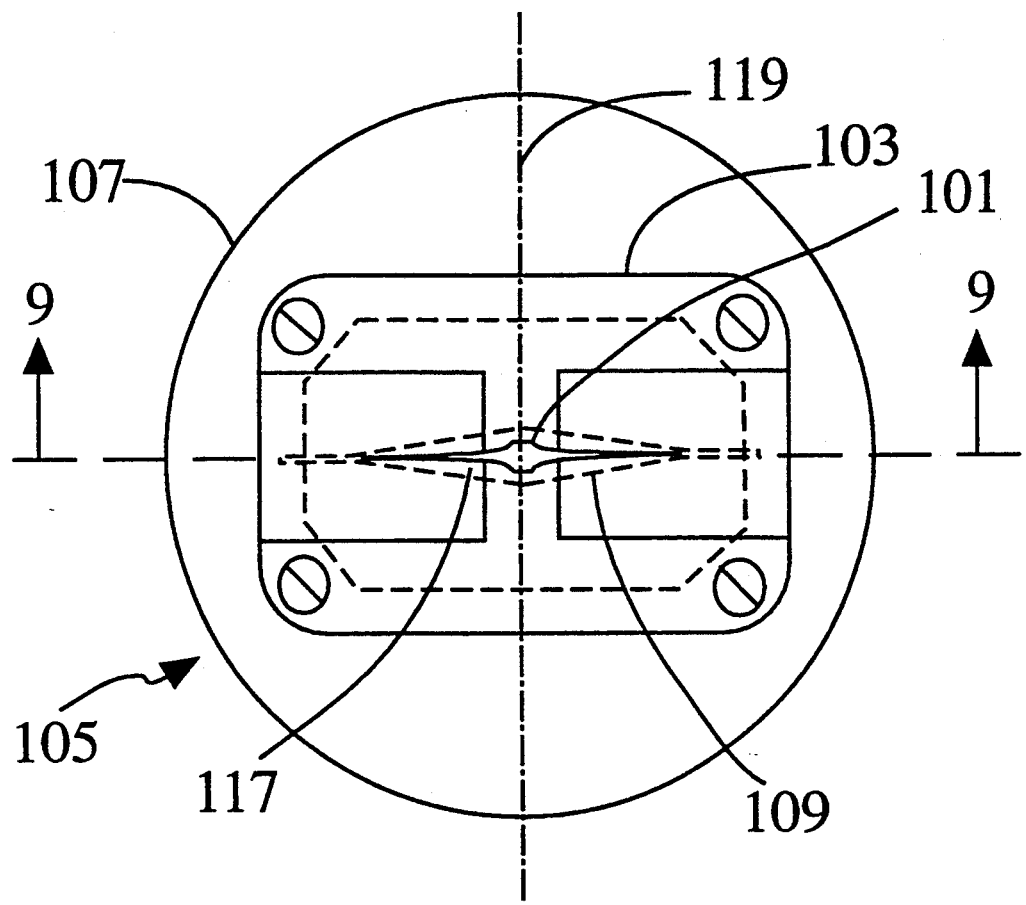
FIGS. 7 and 8 represent a nozzle and impaction plate assembly for a prototype ACGIH respirable particulate mass universal impactor.
Figure 8:
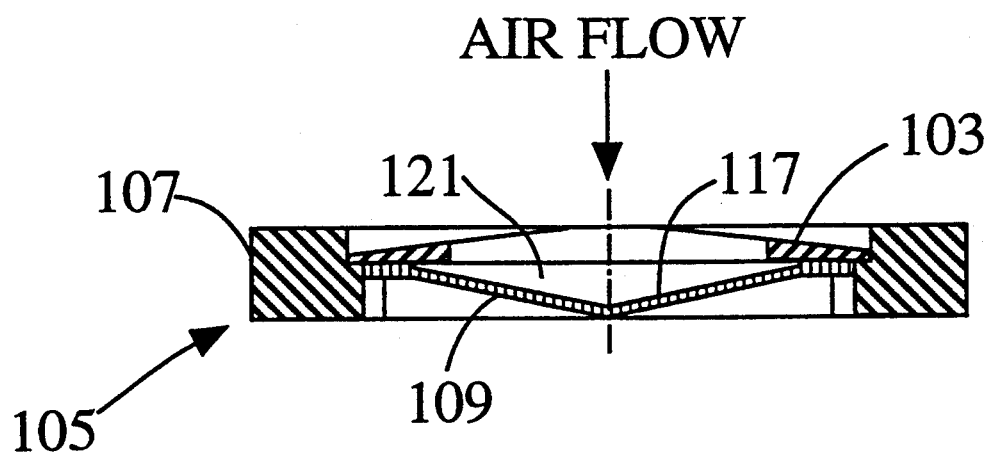

Prior to the cutting of the slit opening, the slit blank 103 is milled so that the thickness is less at the narrow ends 115 of the slit 101, as shown in FIG. 7, to reduce air friction at the narrow ends. The thickness varies from about one slit width at the large end to 13 slit widths at the narrow ends.

The cutpoint of an impactor is insensitive to the slit-to-plate distance, provided the distance is greater than half the slit width. That permits the use of a flat impaction surface 117, sloped from the center 119 so that the distance 121 between the slit 101 and the impaction plate 109 is less at the narrow ends 115 of the slit. The slit-to-plate distance 121 varies from approximately one to three slit widths. The impaction plate 109 has a solid impaction surface 117. The design permits the use of an oil-soaked porous impactor plate to prevent particle bounce. The impaction plate 109 is tapered in the horizontal direction to provide less width at the narrow ends of the slit.

Figure 9:
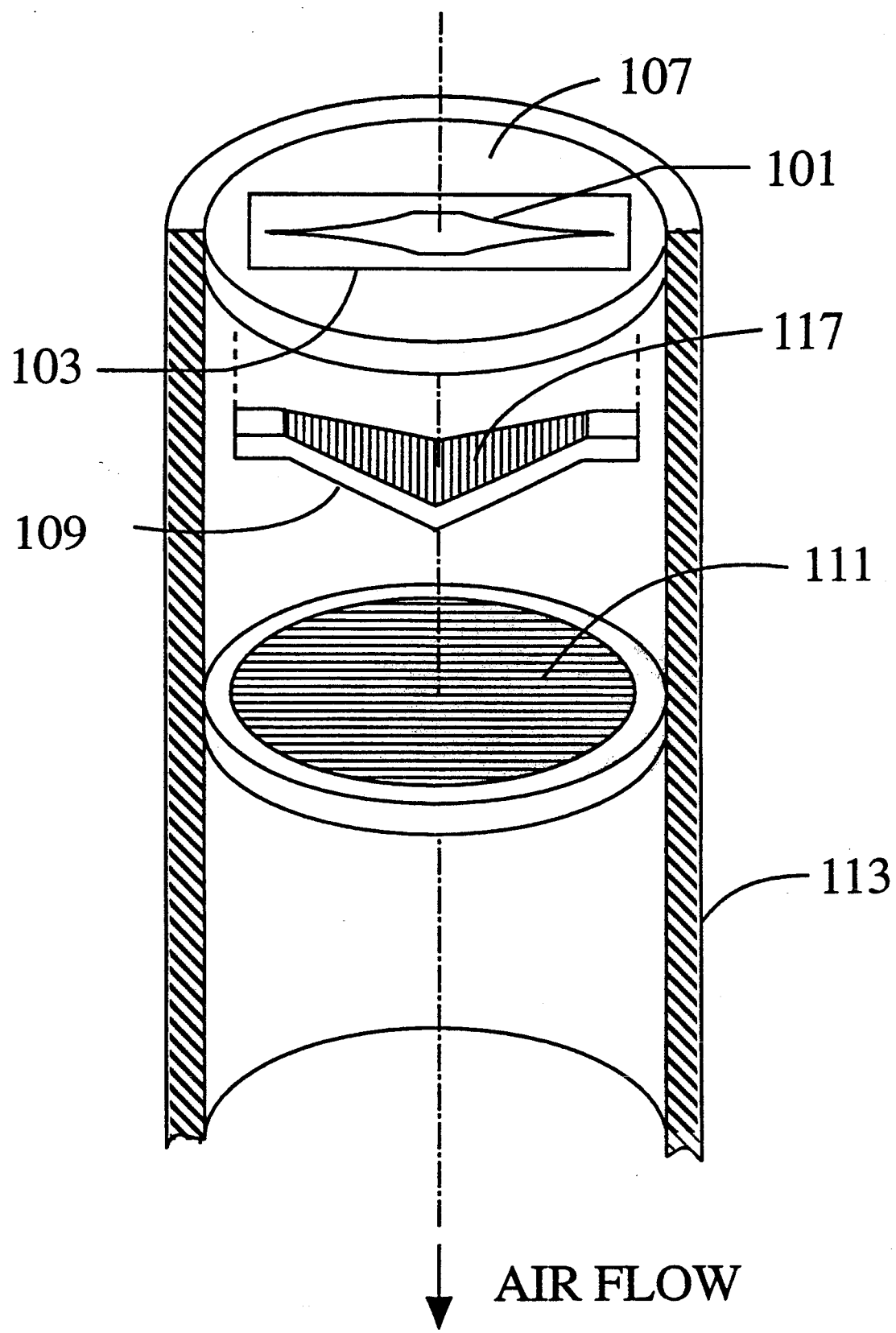
FIG. 9 is a schematic representation of one version of the universal impactor sampler.

Slit plate 103 with slit 101 is held on support disc 107. Support disc 107 is attached to tube support 113 (FIG. 9). Impaction plate 109 having impaction surface 117 is mounted just below slit 101. In FIG. 9 the impaction plate 109 is shown separated from the slit for illustrative purposes. A particle collector 111 is mounted on the tube support below the impaction plate. Tube support 113 conducts the air which passes through the slit and flows around the impaction plate to the particle collector and then to an air mover.

Figure 10:
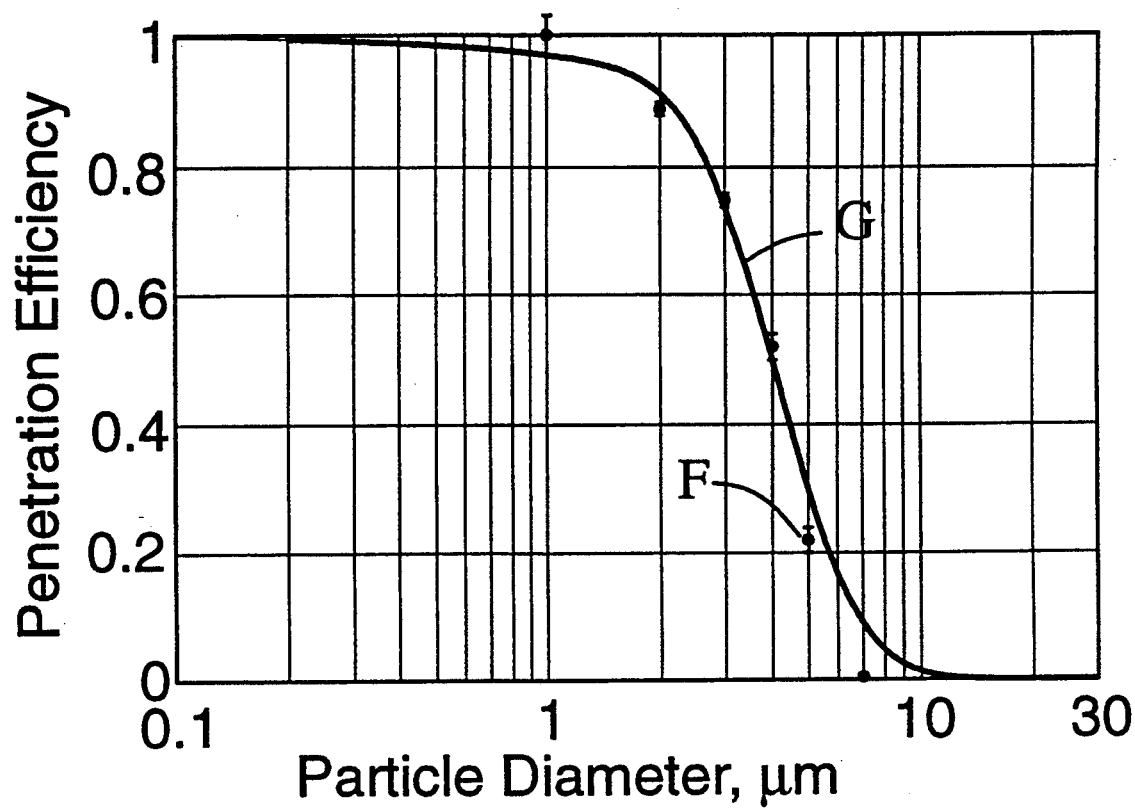
FIG. 10 shows measured penetration efficiency points for the prototype ACGIH respirable particulate mass universal impactor compared to the ACGIH mass criteria line.
Figure 11:
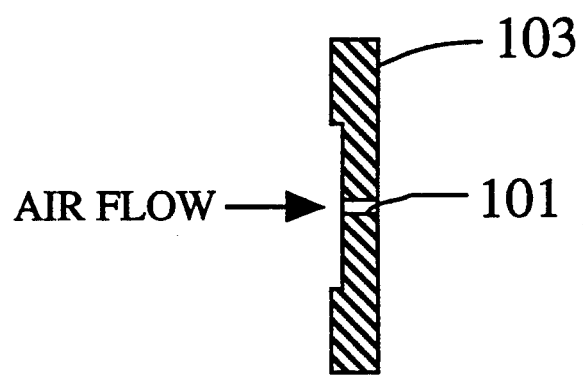
FIG. 11 shows the cross-section of the slit at 11—11 of FIG. 6.

The ACGIH respirable mass universal impactor was tested in the laboratory with monodisperse oleic acid particles. It was determined that the flow rate necessary to obtain a 50% efficiency was 6.2L/min, rather than the planned 4L/min flowrate. All measurements are reported at 6.2L/min. The results are listed in Table 1 and are presented in a graph in FIG. 10. The quoted errors are calculated from the standard deviations of repeated counts. It can be seen that the measurements follow the desired curve closely except at the ends, as expected. The efficiency reaches 0 and 100% at the particle sizes calculated for the truncations. The test generally verifies the invention.

The impactor of the invention has particle collection characteristics conforming to almost any preselected sampling criteria. The impactor has a slit nozzle shaped according to a theoretical determination to produce a collection efficiency smoothly varying with particle diameter to fit the desired curve. An impactor was constructed for sampling the ACGIH respirable mass. Because the ACGIH criteria extends indefinitely to large and small particle diameters, it was necessary to truncate the slit.

The slit is truncated at the narrow end. However, the error caused by the truncation can be made small enough to be acceptable for most practical purposes. The deviation from the criteria is greater at the large particle end. That deviation could be reduced by extending the slit at the large end. That would then require reducing the width. The overall length of the slit could be kept small by eliminating the reflected side of the slit. That would also reduce the flowrate. Criteria such as the BMRC respirable mass and the USEPA PM10 have definite large particle ends and do not require any truncation of the slit.

Collection efficiencies of the prototype impactor measured with oleic acid particles at a flow rate of 6.2L/min. are shown in Table 1. The errors listed are standard deviations of repeated counts.

TABLE 1

| Aerodynamic Diameter, $\mu m$ | Collection Efficiency |
| --- | --- |
| 1 | 1.03 ± 0.01 |
| 2 | 0.89 ± 0.01 |
| 3 | 0.75 ± 0.01 |
| 4 | 0.52 ± 0.02 |
| 5 | 0.22 ± 0.02 |
| 7 | 0.004 ± 0.001 |

While the invention has been described with reference to specific embodiments, modifications and variations of the invention may be constructed without departing from the scope of the invention, which is defined in the following claims.

I claim:

1. Airborne particle sampling apparatus, comprising a slit plate having a tapered slit for passing airborne particles through the slit, and an impaction plate mounted below the slit plate for collecting those particles flowing through the slit and impacting on the impaction plate, and a passage adjacent to the impaction surface allowing particles not impacting to penetrate past the impaction plate, wherein the tapered slit has a taper normal to a direction of particle flow.

2. The apparatus of claim 1, wherein the shape of the tapered slit produces a particle penetration efficiency that varies smoothly with particle size.

3. The apparatus of claim 1, wherein the shape of the tapered slit produces a particle penetration efficiency that conforms to a preselected sampling criteria.

4. The apparatus of claim 1, further comprising means for collecting particles penetrating past the impaction plate.

5. The apparatus of claim 1, further comprising means for sensing particles penetrating past the impaction plate.

6. The apparatus of claim 1, further comprising means for moving the air and airborne particles through the tapered slit and past the impaction plate.

7. The apparatus of claim 1, wherein the tapered slit tapers from a wide end to a narrow end.

8. The apparatus of claim 7, wherein the tapered slit smoothly tapers from a wide end to a narrow end.

9. The apparatus of claim 1, wherein the tapered slit has dimensions of width and length determined by:

(a) $W_k = d_k^2 v\, C\rho_p / (9\mu\, St_{50})$ where $d_k$ = particle cutoff diameter corresponding to the $k^{th}$ equal increment of collection efficiency on a curve of collection efficiency v. particle diameter k = number of the increment $W_k$ = width of the $k^{th}$ increment v = air flow velocity C = Cunningham slip factor $\rho_p$ = particle material density $\mu$ = air viscosity $St_{50}$ = Stokes number corresponding to 50% particle collection (b) $L_k = a/W_k$ where $L_k$ = length of the $k^{th}$ increment a = constant.

10. The apparatus of claim 1, wherein the tapered slit tapers from opposite narrow ends to a central wide part.

11. The apparatus of claim 10, wherein the tapered slit smoothly tapers from remote narrow ends to a central wide part.

12. The apparatus of claim 1, wherein the tapered slit is symmetrical about an axis extending between ends of the tapered slit.

13. The apparatus of claim 1, wherein the tapered slit is symmetrical about an axis perpendicular to an axis extending between ends of the tapered slit.

14. The apparatus of claim 1, wherein the tapered slit has a curved axis extending between ends of the slit.

15. The apparatus of claim 1, wherein the slit plate is bevelled from a thick part having a wide slit opening to a thin part having a narrow slit opening.

16. The apparatus of claim 1, wherein the impaction plate has a sloped impaction surface which is spaced a comparatively greater distance from a wide part of the tapered slit, and a comparatively smaller distance from a narrow part of the tapered slit.

17. The apparatus of claim 1, wherein the impaction plate is relatively wider near a wide part of the tapered slit, and is relatively narrower near a narrow part of the tapered slit.

18. The apparatus of claim 1, further comprising means for sensing particles penetrating past the impaction plate for analysis of size-selected particles.

19. The apparatus of claim 1, further comprising means for sensing particles penetrating past the impaction plate to provide a real time signal of size-selected particle concentration.

20. An impactor for particle sample collection, comprising a support, a slit plate on the support, and a slit in the slit plate, an impaction plate mounted on the support below the slit for collecting particles that impact on the impaction plate, a passage adjacent to the impaction plate to allow particles that do not impact to penetrate past the impaction plate, the slit having a shape and a taper normal to a direction of particle flow for producing a particle penetration efficiency that varies smoothly with particle size.

21. The apparatus of claim 20, wherein the shape of the slit produces a particle penetration efficiency that conforms to preselected sampling criteria.

22. The apparatus of claim 20, wherein the shape of the slit produces a particle penetration efficiency that smoothly follows a preselected particle size-selective sampling criteria.

23. Particle impactor apparatus for an air sampler for separation and collection of airborne particles with an efficiency dependent on particle size following a preselected particle penetration curve, comprising:

a. an impaction plate mounted below a slit plate, said slit having a width tapering along a length of the slit in a direction normal to a direction of particle flow;

b. the impaction plate being mounted below the slit plate for collecting particles flowing through the slit and impacting on the impaction plate; and c. a passage adjacent to an impaction surface of the impaction plate for allowing particles not impacting to penetrate past the impaction plate.

24. The apparatus of claim 23, wherein the slit has dimensions of width and length determined by:

$W_k = d_k^2 v\ C\rho_p/(9\mu\ St_{50})$ where
- $d_k$ = particle cutoff diameter corresponding to the $k^{th}$ equal increment of collection efficiency on a curve of collection efficiency v. particle diameter
- k = number of the increment
- $W_k$ = width of the $k^{th}$ increment
- v = air flow velocity
- c = Cunningham slip factor
- $\rho_p$ = particle material density
- $\mu$ = air viscosity
- $St_{50}$ = Stokes number corresponding to 50% particle collection (b) $L_k = a/W_k$ where
- $L_k$ = length of the $k^{th}$ increment
- a = constant.

25. The apparatus of claim 23, wherein the shape of the tapered slit produces a particle penetration efficiency that varies smoothly with particle size.

26. The apparatus of claim 23, wherein the tapered slit tapers from opposite narrow ends to a central wide part.

27. The apparatus of claim 23, wherein the tapered slit is symmetrical about an axis extending between ends of the tapered slit.

28. The apparatus of claim 23, wherein the tapered slit is symmetrical about an axis perpendicular to an axis extending between ends of the tapered slit.

29. The apparatus of claim 23, wherein the tapered slit has a curved axis extending between ends of the slit.

30. The apparatus of claim 23, wherein the impaction plate has a sloped impaction surface which is spaced a comparatively greater distance from a wide part of the tapered slit, and a comparatively smaller distance from a narrow part of the tapered slit.

31. The apparatus of claim 23, wherein the impaction plate is relatively wider near a wide part of the tapered slit, and is relatively narrower near a narrow part of the tapered slit.

* * * * *